United States Patent
Mogul (10) Patent No.: US 6,246,905 B1
(45) Date of Patent: Jun. 12, 2001

(54) MEDICAL INSTRUMENT THAT SUPPLIES MULTIPLE ENERGY FORMS

(76) Inventor: Jamil Ahmad Mogul, 2665 Somerset Park Cir., San Jose, CA (US) 95132

( * ) Notice: Subject to any disclaimer, the term of this patent is extended or adjusted under 35 U.S.C. 154(b) by 0 days.

(21) Appl. No.: 09/364,568

(22) Filed: Jul. 30, 1999

(51) Int. Cl.[7] .................................................. A61B 19/02
(52) U.S. Cl. ................................................................ 607/3
(58) Field of Search ................................ 601/15; 604/20; 606/37, 42; 607/1, 2, 3, 10, 66; 128/897

(56) References Cited

U.S. PATENT DOCUMENTS

| 3,219,029 | * | 11/1965 | Richards et al. | ........................ 607/66 |
| 5,399,007 | * | 3/1995 | Marconet | ................................. 607/2 |
| 5,678,568 | * | 10/1997 | Uchikubo et al. | .................... 128/697 |
| 6,022,327 | * | 2/2000 | Chang | ..................................... 201/15 |

* cited by examiner

*Primary Examiner*—William E. Kamm
(74) *Attorney, Agent, or Firm*—The Kline Law Firm (57) ABSTRACT

A multiple energy form supply device is intended for medical use in minimally invasive and general surgery applications. The device includes a plurality of energy supply modules mounted in a movable cart. The device will also typically include a computer control means, with a central PCB that is in communication with the energy supply modules. The device will also have at least one display to aid in the operation of the device, data input mechanisms to allow various means of control of the modules, and data output devices to display and store pertinent information relative to the operation of the device.

12 Claims, 7 Drawing Sheets

MEDICAL INSTRUMENT THAT SUPPLIES MULTIPLE ENERGY FORMS

FIELD OF THE INVENTION

The present invention relates generally to medical equipment, and more particularly is a portable unit that supplies a plurality of energy forms adapted for medical treatments.

BACKGROUND OF THE INVENTION

Over the years, a large number of medical instruments have been designed with the intention of aiding physicians in their treatment of patients. One area of medical treatment that is highly dependent on mechanical equipment is the application of various forms of energy to the patient's body. Depending on the course of treatment, a doctor might require one or more of a large number of energy sources, examples being laser, ultrasonic, radiofrequency, microwave, mechanical, and pneumatic.

Each of these energy sources can be quite beneficial to a medical practitioner in his treatment of a patient. However, one of the drawbacks to current art machinery is that a separate machine is required to supply each type of energy. Using separate machines for the delivery of each of these energy types leads to a very high capital expense, as well as creating a storage problem. If the machines are kept in the treatment area, which is of course desirable for convenience of access, the treatment area can easily become quite cluttered, thereby making movement in the area difficult and even potentially dangerous.

Accordingly, it is an object of the present invention to provide piece of medical equipment that is able to deliver a plurality of energy forms from a single machine.

It is a further object of the present invention to provide a device that is modular so that the various energy supply modules are very easily replaced, substituted, and removed for repair.

It is a still further object of the present invention to provide a computerized control means for the device, and for storage of data relevant to the treatment of the patient.

SUMMARY OF THE INVENTION

The present invention is a multiple energy form supply device intended for medical use in minimally invasive and general surgery applications. The device comprises a plurality of energy supply modules mounted in a movable cart. The device will also typically include a computer control means, with a central PCB that is in communication with the energy supply modules.

The device will also have at least one display means to aid in the operation of the device, data input means to allow various means of control of the modules, and data output means to display and store pertinent information relative to the operation of the device.

An advantage of the present invention is that it allows a medical practitioner to have access to a plurality of energy forms via a single machine.

Another advantage of the present invention is that it greatly reduces the capital outlay required of the practitioner or of the medical facility obtaining the device.

A still further advantage of the present invention is that the modular design of the device enables it to be easily conformed to a user's specific needs.

These and other objects and advantages of the present invention will become apparent to those skilled in the art in view of the description of the best presently known mode of carrying out the invention as described herein and as illustrated in the drawings.

DETAILED DESCRIPTION OF THE INVENTION

The present invention is a multiple energy form supply device 10. The multiple energy form supply device 10 is intended for medical use in minimally invasive and general surgery applications.

Figure 1:
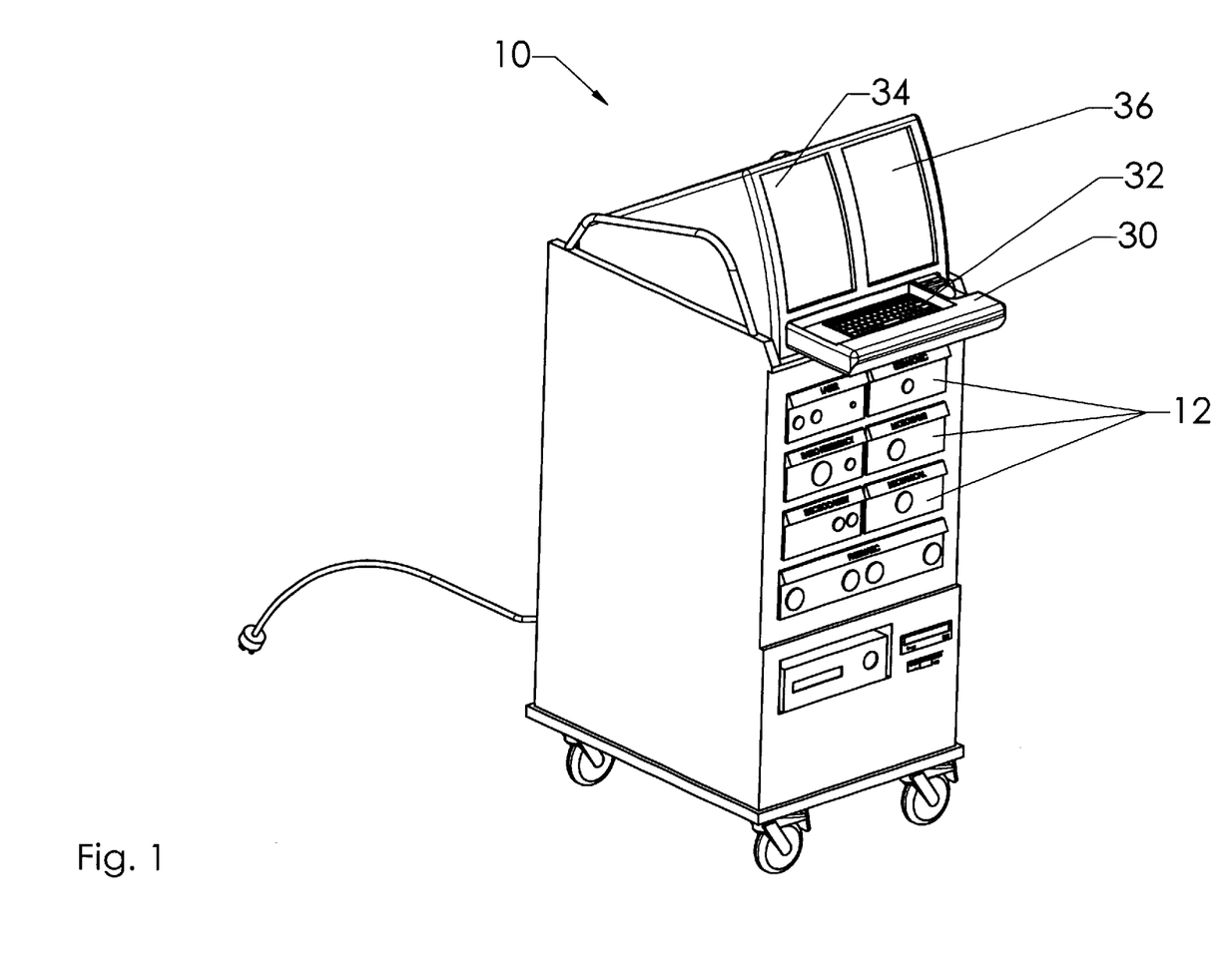
FIG. 1 is a perspective view of the multiple energy form supply device of the present invention.
Figure 2:
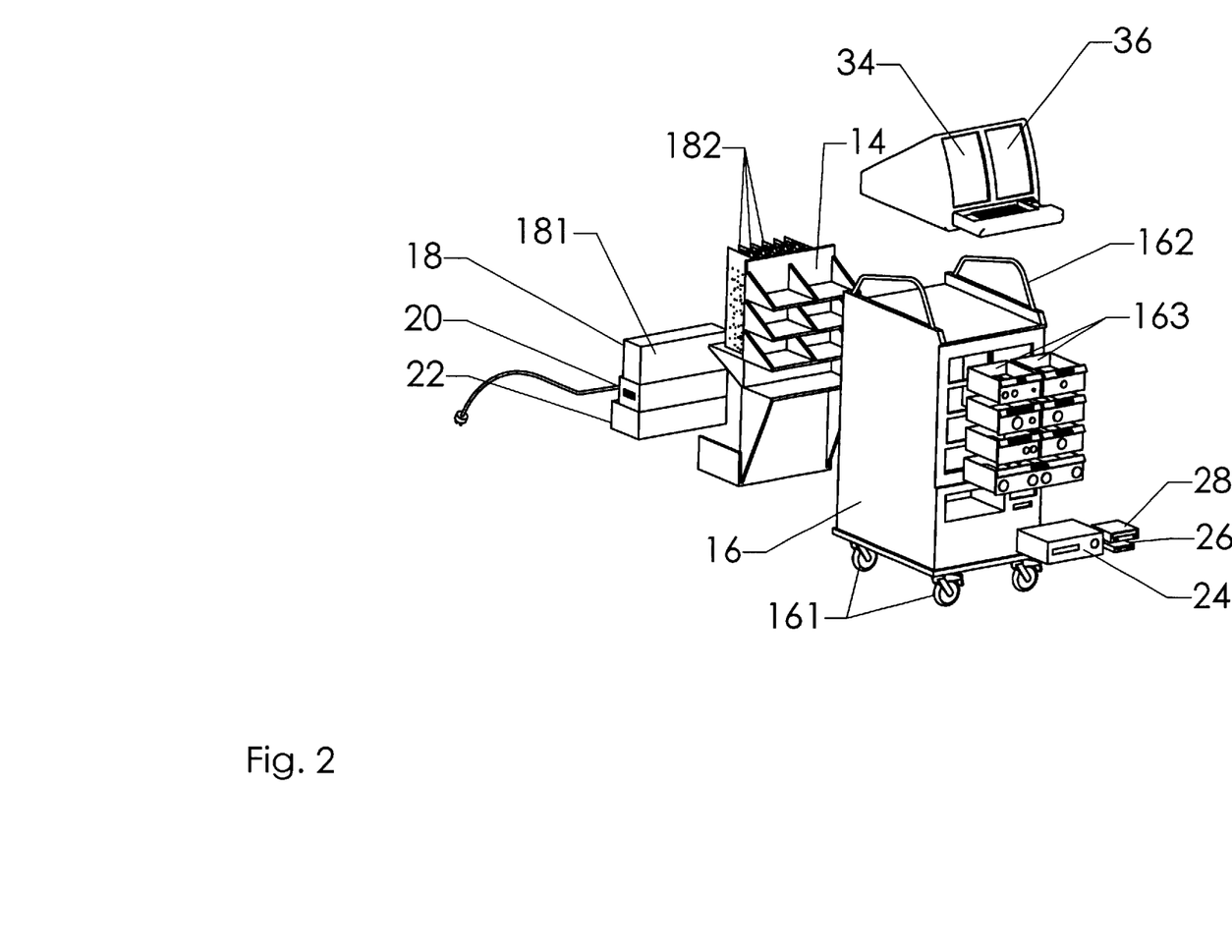
FIG. 2 is an exploded view of the multiple energy form supply device of the present invention.
Figure 3:
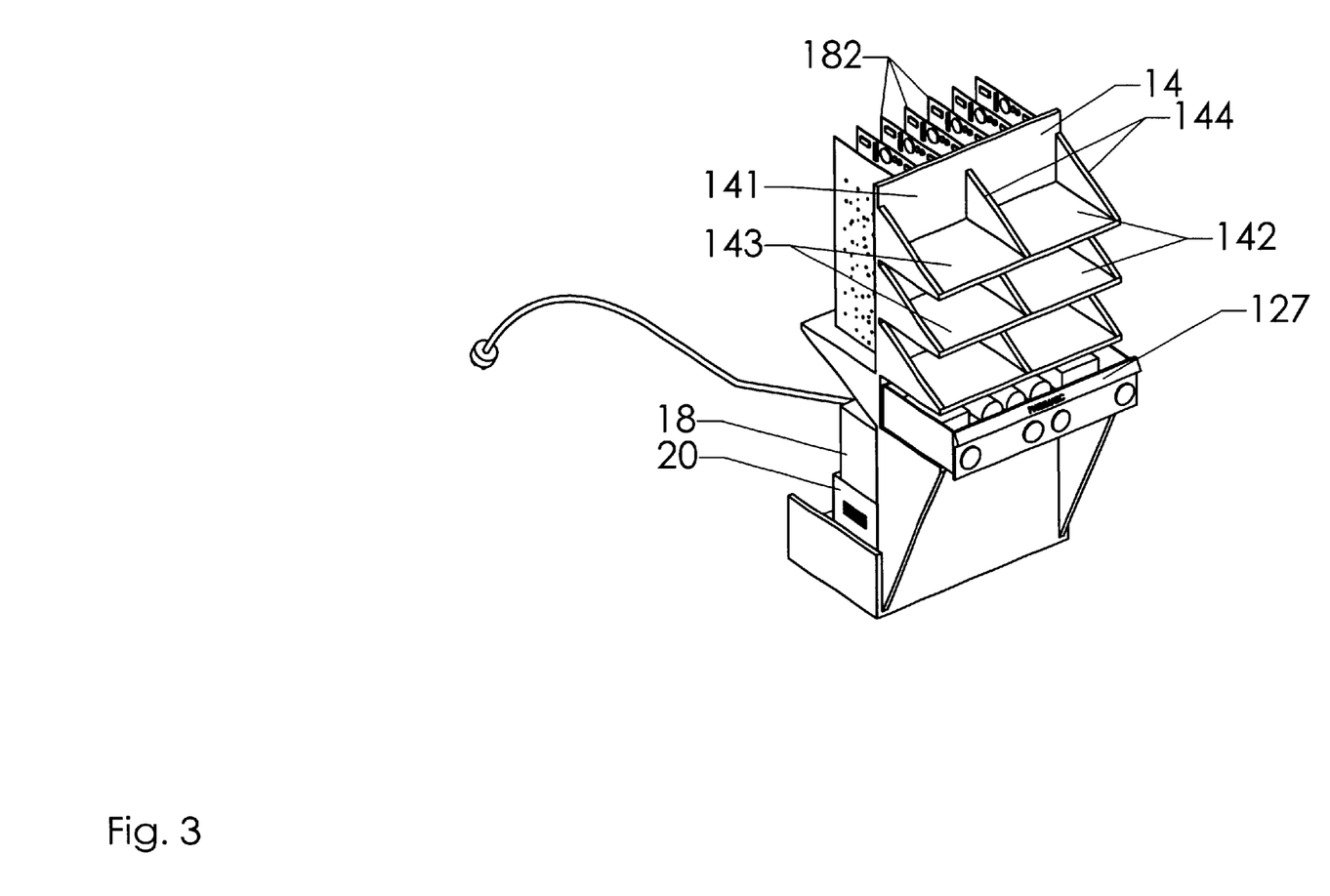
FIG. 3 illustrates the mounting infrastructure with the interface electronics PCB and a single energy module installed.
Figure 4:
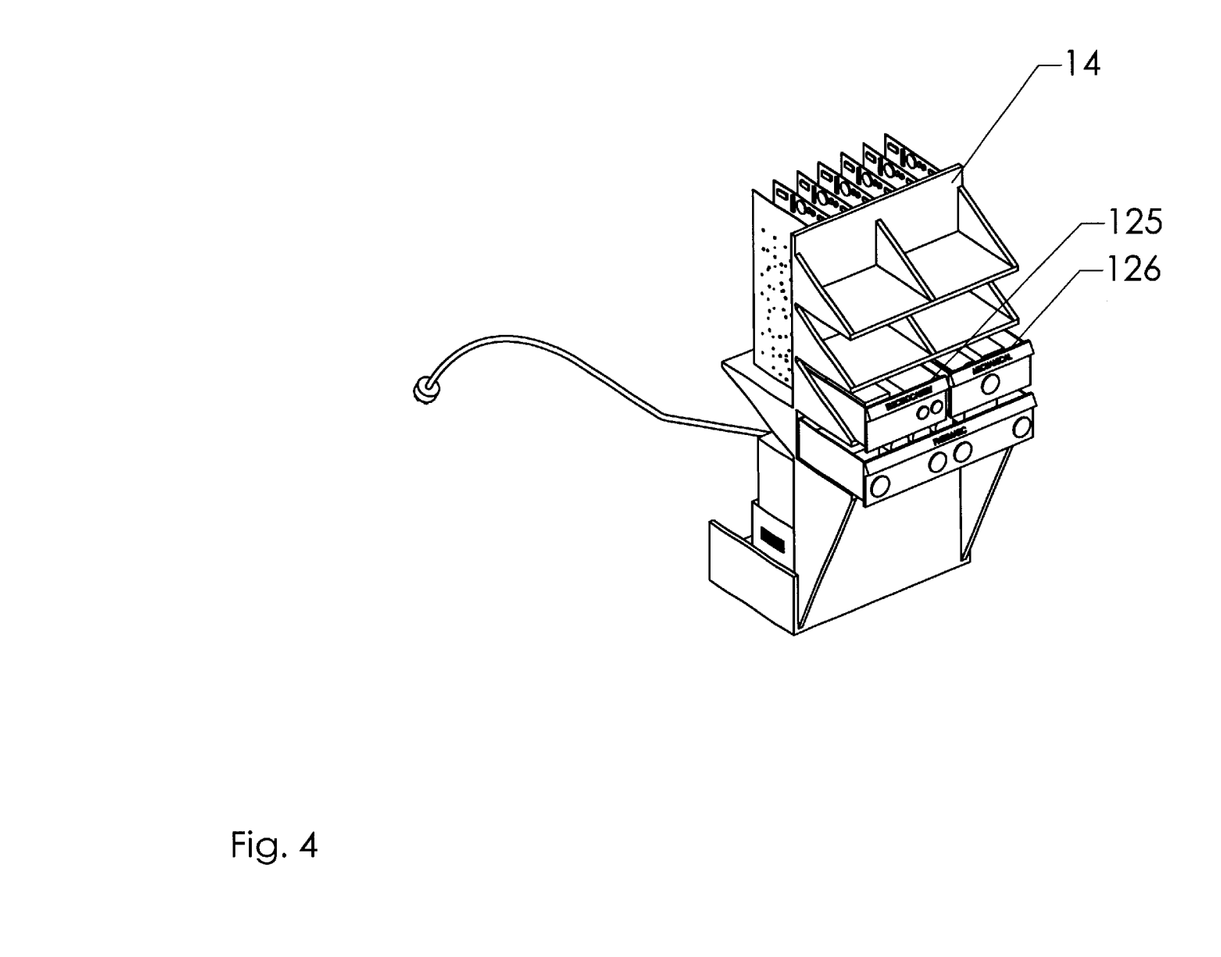
FIG. 4 shows the mounting infrastructure with the interface electronics PCB and two energy modules installed.
Figure 5:
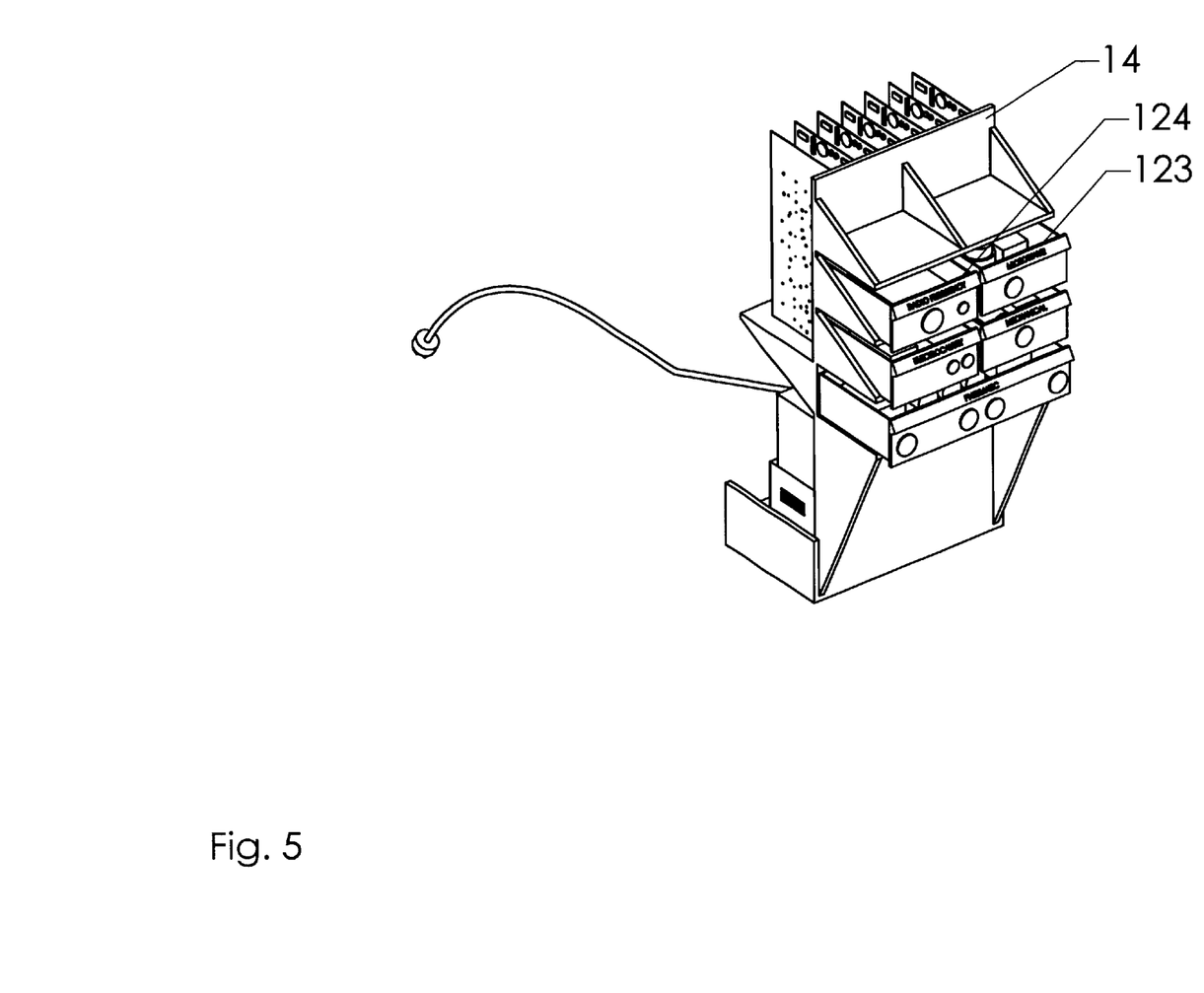
FIG. 5 depicts the mounting infrastructure with the interface electronics PCB and three energy modules installed.
Figure 6:
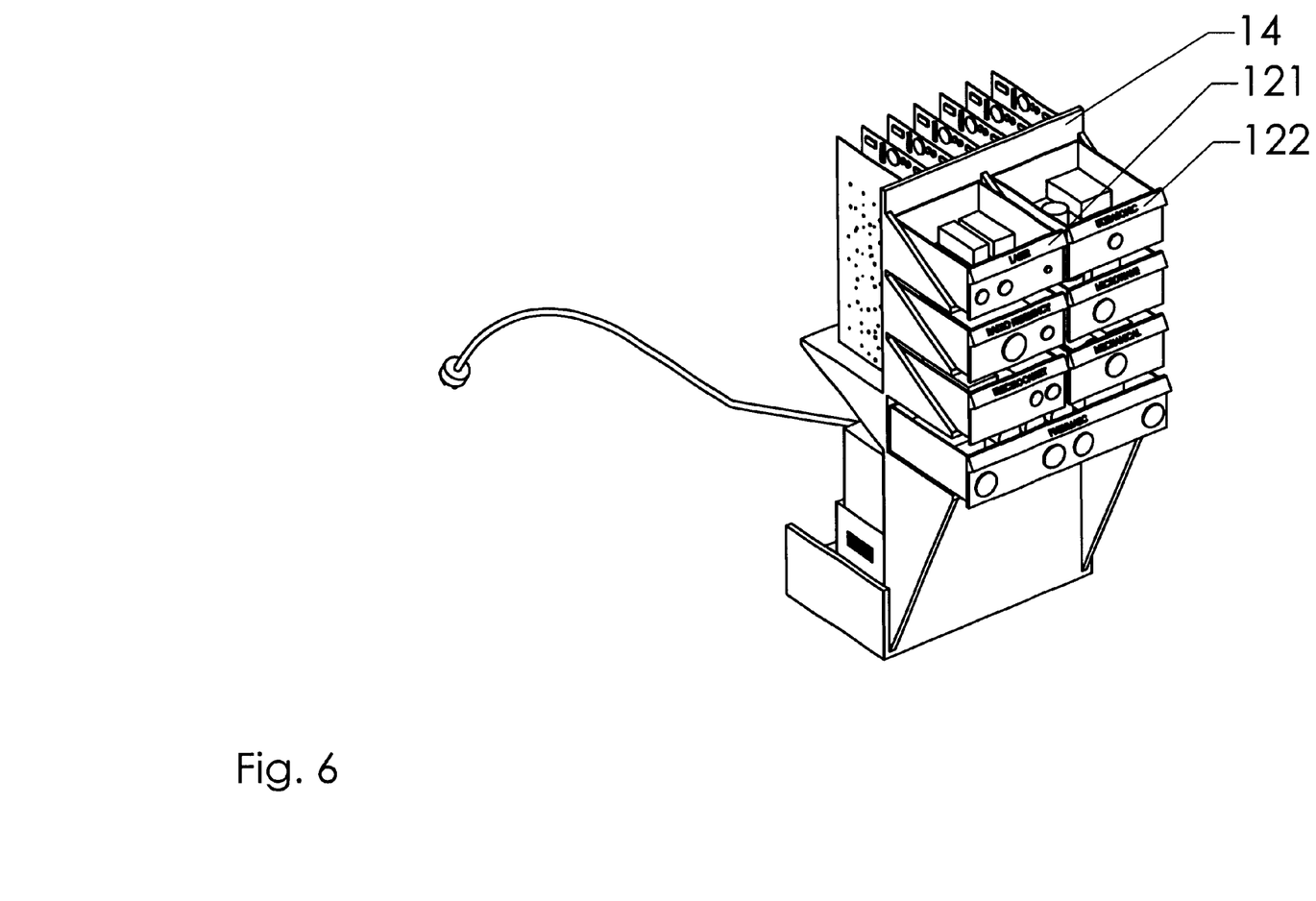
FIG. 6 shows the mounting infrastructure with the interface electronics PCB and two energy modules installed.

Components of the multiple energy form supply device 10 include a plurality of energy supply modules 12 installed in a mounting infrastructure 14 that is contained in an exterior housing 16. A main device controller and computer system 18, a cooling means 20, and a power supply 22 are also secured in the mounting infrastructure 14. To aid the user in his utilization of the device, the mounting infrastructure 14 also includes areas adapted to receive various read/write device including a VCR 24, a floppy disk drive 26, and a DVD drive 28. The device is controlled and various required data is entered via input means including a keyboard 30 and mouse or trackball 32. Visual output is displayed on a pair of CRT's, a first CRT being utilized as a graphic user interface (GUI) 34, and a second CRT being used as a video display 36.

Referring now primarily to FIG. 2, the exterior housing 16 is designed to allow the device 10 to be easily moved about. The housing 16 includes a plurality of wheels or casters 161 mounted on the bottom side of the housing 16. Handles 162 provide a means for a user to easily grip the device 10 for movement. A front side of the exterior housing 16 includes a plurality of access openings 163 that allow the user to easily reach the various energy supply modules 12. Access openings 163 are also provided for the read/write devices such as the VCR 24, the floppy disk drive 26, and the DVD drive 28.

The mounting infrastructure 14 is secured within the interior of the housing 16. The mounting infrastructure 14 includes an upright central partition 141. Affixed to a front side of the partition 141 are a plurality of module receptacles 142. The module receptacles 142 each include at least one horizontal member 143 that provides the support surface for the module 12 that is placed in the receptacle 142. For added strength and stability, the module receptacles 142 may also include one or more vertical support members 144. The support members 144 are attached to both the central partition 141 and the horizontal members 143. When the mounting infrastructure 14 is secured in the exterior housing 16, an open area of the module receptacles 142 is exposed at a front side of the device 10.

It is envisioned that among the plurality of energy modules 12 available for selection by the user will be at least a laser module 121, an ultrasonic module 122, a microwave module 123, a first radiofrequency module 124, a second radiofrequency module 125, a mechanical module 126, and a pneumatic module 127. The functions of is the laser module 121, the ultrasonic module 122, and the microwave module 123 are self-evident. The first RF module 124 is used to supply an energy source for ablation, and the second RF module 125 supplies an energy source for electrocautery. The mechanical module 126 is a motor unit that provides a driving force for mechanical surgical tools. The pneumatic module 127 supplies compressed air to power pneumatic surgical tools. Each of the modules 12 includes on its front face at least one plug receptacle to receive a probe or similar tool used with the module. The front face of the modules 12 is accessible from the front of the device 10 through the openings in the front of the exterior housing 16.

Also exposed on the front side of the device 10 are the read/write devices, which will typically include at least the VCR 24, the floppy disk drive 26, and the DVD drive 28. In addition to providing a convenient means of storing date, the read/write devices can be used to provide instructional and/or operational information on the video display 36.

The rear side of the central partition 141 includes a receiving area in which the main device controller and computer system 18, the cooling means 20 (which will be required for at least the laser module 121), and the power supply 22 are contained. These elements are situated in the rear of the device because access to them should rarely be required.

The main device controller and computer system 18 includes a main CPU 181 for the computer control of the device 10. If desired by the user, some or all of the circuitry of the main device controller and computer system 18 may be included on a PCB that serves as the central partition 141. In addition, an interface electronics PCB 182 for each energy module 12 installed in the device 10 is mounted above the CPU 181. Each of the interface electronics PCB's 182 controls the operation of its corresponding energy module 12. Operation of the main device controller and computer system 18 is best understood with reference to FIG. 7, which is a flow chart illustrating the computer control system 18 of the device 10.

Figure 7:
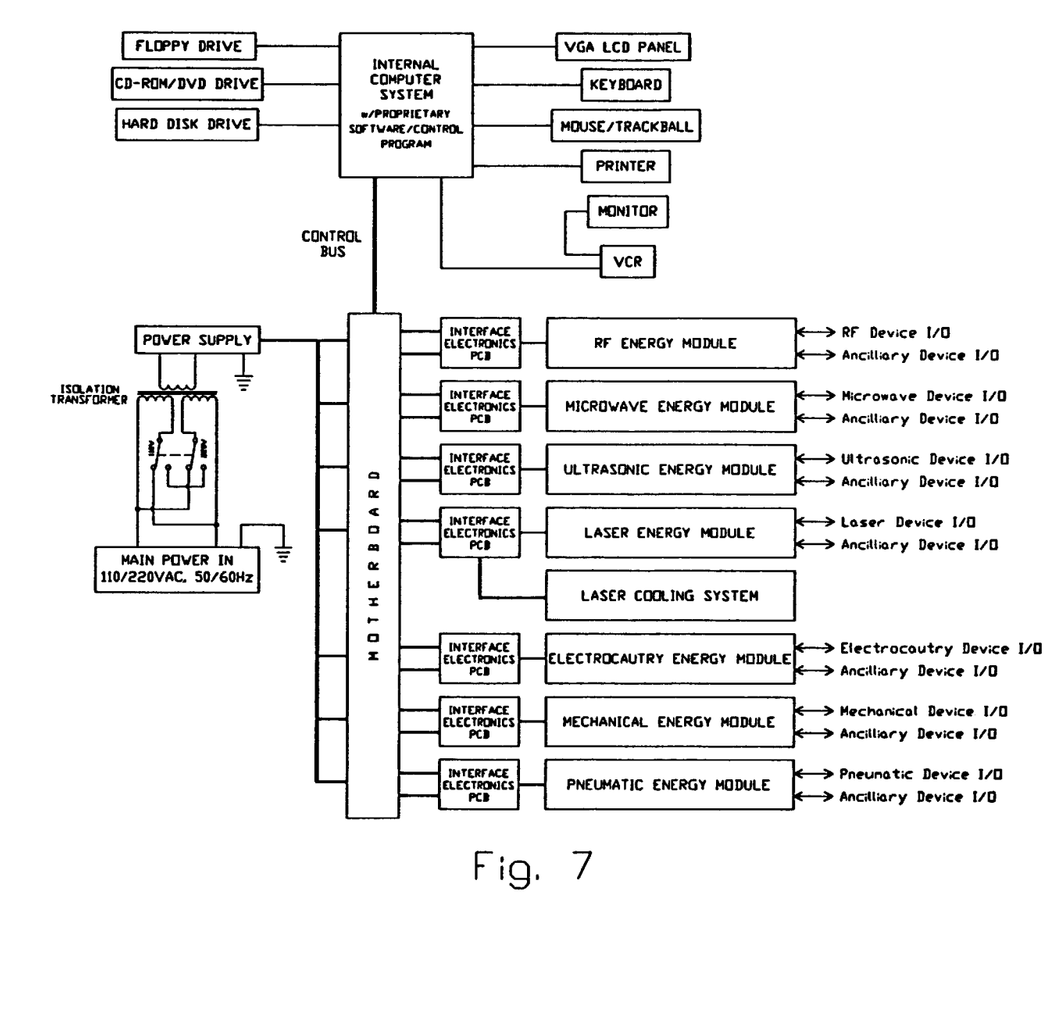
FIG. 7 is a flow chart illustrating the computer control system of the device.

When the device 10 is powered on, the GUI 34 displays a menu of the various functions available to the user. Typically, the menu will include at least a choice of operational modes (manual or automatic), service/test mode, function icons, reading/storing information, an operational information about the device itself.

When one of the energy supply modules 12 installed in the device 10 is activated, a GUI screen specific to that module will be displayed on the GUI 34. That screen will include operating information for the specific probe and/or sensors being utilized with the supply module. The screen will also include menus that allow adjustment of the parameters that control the operation of the module, i.e. appropriate power supply for the energy form desired. If the module or the probe does include a sensor that is collecting data, that data will also be displayed on the GUI 34.

Each of the energy supply modules 12, through their respective interface electronics PCB's 182, is controlled by the CPU 181 of the main controller and computer system 18. The main controller and computer system 18 also allows the energy supply modules 12 to be in communication with the various 10 devices, the VCR 24, the floppy disk drive 26, and the DVD drive 28. In this manner, information retrieved through the various sensors of the modules 12 or the probes can be easily stored for future reference and use. The stored information is readily available to determine appropriate settings and procedures for successive treatments.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A multiple energy form supply device comprising:
a plurality of energy supply modules,
a mounting infrastructure,
an exterior housing with an interior opening to receive said mounting infrastructure, said exterior housing includes a plurality of openings on a front side thereof,
a main device controller and computer system, and
a power supply; wherein
said mounting infrastructure comprises an upright central partition, affixed to a front side of said partition are a plurality of module receptacles with open faces, said module receptacles each include at least one horizontal member that extends outward from said central partition, said horizontal member provides a support surface to receive at least one of said energy supply modules, said mounting infrastructure is secured in said interior opening of said exterior housing such that said open faces of said module receptacles are in communication with said openings on said front side of said exterior housing.

2. The multiple energy form supply device as defined in claim 1 wherein:
said module receptacles include at least one vertical support member, said vertical support member is attached to both said central partition and said horizontal member, such that strength and stability of said horizontal member is increased.

3. The multiple energy form supply device as defined in claim 1 wherein:
said device further comprises at least one read/write device in communication with said main device controller and computer system.

4. The multiple energy form supply device as defined in claim 1 wherein:
said device further comprises a computer control means to control power distribution to and operation of said energy supply modules.

5. The multiple energy form supply device as defined in claim 1 wherein:
said device further comprises an interface electronics printed circuit board for each said energy supply module, each said interface electronics printed circuit board providing the communication link between a respective said energy supply module and a computer control means.

6. The multiple energy form supply device as defined in claim 1 wherein:
at least one of said energy supply modules uses a high level of energy, and said device further comprises a cooling system that dissipates heat generated by energy supply modules that use high levels of energy.

7. A multiple energy form supply device comprising:

a plurality of energy supply modules, a mounting infrastructure, an exterior housing with an interior opening to receive said mounting infrastructure, said exterior housing includes a plurality of openings on a front side thereof, a main device controller and computer system, and a power supply; wherein said mounting infrastructure comprises an upright central partition, affixed to a front side of said partition are a plurality of module receptacles with open faces, said module receptacles each include at least one horizontal member that extends outward from said central partition, said horizontal member provides a support surface to receive at least one of said energy supply modules, said mounting infrastructure is secured in said interior opening of said exterior housing such that said open faces of said module receptacles are in communication with said openings on said front side of said exterior housing, and said energy supply modules comprise a laser module, an ultrasonic module, a microwave module, a first radiofrequency module, a second radiofrequency module, a mechanical module, and a pneumatic module.

8. The multiple energy form supply device as defined in claim 7 wherein:

said module receptacles include at least one vertical support member, said vertical support member is attached to both said central partition and said horizontal member, such that strength and stability of said horizontal member is increased.

9. The multiple energy form supply device as defined in claim 7 wherein:

said device further comprises at least one read/write device in communication with said main device controller and computer system.

10. The multiple energy form supply device as defined in claim 7 wherein:

said device further comprises a computer control means to control power distribution to and operation of said energy supply modules.

11. The multiple energy form supply device as defined in claim 7 wherein:

said device further comprises an interface electronics printed circuit board for each said energy supply module, each said interface electronics printed circuit board providing the communication link between a respective said energy supply module and a computer control means.

12. The multiple energy form supply device as defined in claim 7 wherein:

at least one of said energy supply modules uses a high level of energy, and said device further comprises a cooling system for energy supply modules that dissipates heat generated by energy supply modules that use high levels of energy.

* * * * *